United States Patent
Kwon et al.

(10) Patent No.: US 12,274,174 B2
(45) Date of Patent: Apr. 8, 2025

(54) SYSTEMS AND METHODS FOR INTEGRATING ULTRASONIC TRANSDUCERS WITH HYBRID CONTACTS

(71) Applicant: eXo Imaging, Inc., Redwood City, CA (US)

(72) Inventors: Haesung Kwon, Austin, TX (US); Brian Bircumshaw, Oakland, CA (US); Sandeep Akkaraju, Wellesley, MA (US)

(73) Assignee: Exo Imaging, Inc., Santa Clara, CA (US)

(*) Notice: Subject to any disclaimer, the term of this patent is extended or adjusted under 35 U.S.C. 154(b) by 756 days.

(21) Appl. No.: 17/159,538

(22) Filed: Jan. 27, 2021

(65) Prior Publication Data
US 2021/0151661 A1   May 20, 2021

Related U.S. Application Data

(63) Continuation of application No. PCT/US2019/044528, filed on Jul. 31, 2019.

(60) Provisional application No. 62/713,272, filed on Aug. 1, 2018.

(51) Int. Cl.
| | |
|---|---|
| *B06B 1/06* | (2006.01) |
| *B06B 1/02* | (2006.01) |
| *H01L 41/047* | (2006.01) |
| *H10N 30/06* | (2023.01) |
| *H10N 30/80* | (2023.01) |
| *H10N 30/87* | (2023.01) |

(52) U.S. Cl.
CPC ......... *H10N 30/875* (2023.02); *B06B 1/0207* (2013.01); *B06B 1/0622* (2013.01); *B06B 1/0666* (2013.01); *H10N 30/06* (2023.02); *H10N 30/802* (2023.02)

(58) Field of Classification Search
CPC .. H10N 30/875; H10N 30/802; B06B 1/0207; B06B 1/0622; B06B 1/0666
USPC .......................................... 310/322, 334, 335
See application file for complete search history.

(56) References Cited

U.S. PATENT DOCUMENTS

| | | | |
|---|---|---|---|
| 2,808,522 A | 10/1957 | Dranetz | |
| 3,088,323 A | 5/1963 | Walter et al. | |
| 4,156,800 A | 5/1979 | Sear et al. | |
| (Continued) | | | |

FOREIGN PATENT DOCUMENTS

| | | |
|---|---|---|
| CN | 1445872 A | 10/2003 |
| CN | 102577436 A | 7/2012 |
| (Continued) | | |

OTHER PUBLICATIONS

U.S. Appl. No. 17/180,308 Office Action dated Dec. 10, 2021.
(Continued)

*Primary Examiner* — Derek J Rosenau
(74) *Attorney, Agent, or Firm* — Morgan, Lewis & Bockius LLP

(57) ABSTRACT

Disclosed herein are ultrasonic transducer systems with hybrid contacts comprising: an ultrasonic transducer element comprising a substrate and a membrane; an electrical circuitry; and one or more contacts connected to the ultrasonic transducer element and the electrical circuitry, wherein the one or more contacts are: designed geometrically using a set of rules; arranged with respect to the membrane based on the set of rules or a second set of rules, or both.

20 Claims, 9 Drawing Sheets

(56) References Cited

U.S. PATENT DOCUMENTS

| | | |
|---|---|---|
| 4,211,949 A | 7/1980 | Brisken et al. |
| 4,375,042 A | 2/1983 | Marcus |
| 4,445,063 A | 4/1984 | Smith |
| 4,517,842 A | 5/1985 | Twomey et al. |
| 4,630,465 A | 12/1986 | Hatton |
| 4,654,554 A | 3/1987 | Kishi |
| 4,668,906 A | 5/1987 | Ekstrand |
| 4,709,360 A | 11/1987 | Martin et al. |
| 5,488,956 A | 2/1996 | Bartelt et al. |
| 5,520,187 A | 5/1996 | Snyder |
| 5,548,564 A | 8/1996 | Smith |
| 5,825,117 A | 10/1998 | Ossmann et al. |
| 5,945,770 A | 8/1999 | Hanafy |
| 6,051,895 A | 4/2000 | Mercier |
| 6,108,121 A | 8/2000 | Mansell et al. |
| 7,382,635 B2 | 6/2008 | Noda |
| 7,532,093 B1 | 5/2009 | Pulskamp et al. |
| 8,004,158 B2 | 8/2011 | Hielscher |
| 8,626,295 B2 | 1/2014 | Doron et al. |
| 9,067,779 B1 | 6/2015 | Rothberg et al. |
| 9,479,875 B2 | 10/2016 | Hall et al. |
| 10,106,397 B1 | 10/2018 | Kim et al. |
| 10,648,852 B2 | 5/2020 | Akkaraju et al. |
| 10,656,007 B2 | 5/2020 | Akkaraju et al. |
| 10,969,270 B2 | 4/2021 | Akkaraju et al. |
| 2002/0109436 A1 | 8/2002 | Peng et al. |
| 2003/0102777 A1* | 6/2003 | Kuniyasu ............... B06B 1/0629 310/334 |
| 2004/0039246 A1 | 2/2004 | Gellman et al. |
| 2004/0085858 A1 | 5/2004 | Khuri-Yakub et al. |
| 2005/0134574 A1 | 6/2005 | Hill |
| 2005/0146247 A1 | 7/2005 | Fisher et al. |
| 2005/0148132 A1 | 7/2005 | Wodnicki |
| 2005/0200242 A1 | 9/2005 | Degertekin |
| 2006/0043843 A1* | 3/2006 | Sugiura ................... G01S 7/521 310/348 |
| 2006/0113866 A1 | 6/2006 | Ganor |
| 2007/0103697 A1 | 5/2007 | Degertekin |
| 2007/0197922 A1 | 8/2007 | Bradley et al. |
| 2007/0205698 A1 | 9/2007 | Chaggares et al. |
| 2008/0009741 A1 | 1/2008 | Hyuga |
| 2008/0048211 A1 | 2/2008 | Khuri-Yakub et al. |
| 2009/0001853 A1 | 1/2009 | Adachi et al. |
| 2009/0250729 A1 | 10/2009 | Lemmerhirt et al. |
| 2010/0168583 A1 | 7/2010 | Dausch et al. |
| 2010/0225204 A1 | 9/2010 | Hamann et al. |
| 2010/0256501 A1 | 10/2010 | Degertekin |
| 2010/0301227 A1 | 12/2010 | Muntean |
| 2010/0327695 A1 | 12/2010 | Goel et al. |
| 2011/0051461 A1 | 3/2011 | Buchwald et al. |
| 2011/0218594 A1 | 9/2011 | Doron et al. |
| 2012/0091543 A1 | 4/2012 | Torashima et al. |
| 2012/0103096 A1 | 5/2012 | Kandori |
| 2012/0127136 A1 | 5/2012 | Schneider et al. |
| 2012/0187508 A1 | 7/2012 | Adler et al. |
| 2012/0206014 A1 | 8/2012 | Bibl et al. |
| 2012/0250454 A1 | 10/2012 | Rohling et al. |
| 2012/0289897 A1 | 11/2012 | Friend et al. |
| 2012/0319174 A1 | 12/2012 | Wang |
| 2013/0039147 A1 | 2/2013 | Witte et al. |
| 2013/0234559 A1 | 9/2013 | Ermolov |
| 2013/0293065 A1 | 11/2013 | Hajati et al. |
| 2013/0294201 A1 | 11/2013 | Hajati |
| 2013/0331705 A1 | 12/2013 | Fraser |
| 2014/0019072 A1 | 1/2014 | Alles |
| 2014/0117812 A1 | 5/2014 | Hajati |
| 2014/0145561 A1 | 5/2014 | Jin et al. |
| 2014/0219063 A1 | 8/2014 | Hajati et al. |
| 2014/0220723 A1 | 8/2014 | Liu et al. |
| 2014/0225476 A1 | 8/2014 | Degertekin et al. |
| 2014/0328504 A1 | 11/2014 | Stephanou et al. |
| 2015/0097468 A1 | 4/2015 | Hajati et al. |
| 2015/0250452 A1 | 9/2015 | Jin et al. |
| 2015/0265245 A1 | 9/2015 | Von Ramm et al. |
| 2016/0027991 A1 | 1/2016 | Suzuki |
| 2016/0045935 A1 | 2/2016 | Yoon et al. |
| 2016/0105748 A1 | 4/2016 | Pal et al. |
| 2016/0107194 A1 | 4/2016 | Panchawagh et al. |
| 2016/0136686 A1 | 5/2016 | Brock-Fisher |
| 2016/0136687 A1 | 5/2016 | Lewis, Jr. et al. |
| 2016/0262725 A1 | 9/2016 | Boser et al. |
| 2017/0021391 A1 | 1/2017 | Guedes et al. |
| 2017/0043375 A1 | 2/2017 | Weekamp et al. |
| 2017/0209121 A1 | 7/2017 | Davis, Sr. et al. |
| 2017/0232474 A1 | 8/2017 | Oralkan et al. |
| 2017/0309808 A1 | 10/2017 | Hada et al. |
| 2017/0319180 A1 | 11/2017 | Henneken et al. |
| 2017/0322290 A1 | 11/2017 | Ng et al. |
| 2017/0368574 A1 | 12/2017 | Sammoura et al. |
| 2018/0153510 A1 | 6/2018 | Haque et al. |
| 2018/0153512 A1 | 6/2018 | Akkaraju et al. |
| 2019/0176193 A1 | 6/2019 | Shulepov et al. |
| 2019/0316957 A1 | 10/2019 | Akkaraju et al. |
| 2019/0316958 A1 | 10/2019 | Akkaraju et al. |
| 2020/0205776 A1 | 7/2020 | Dekker et al. |
| 2020/0249079 A1 | 8/2020 | Akkaraju et al. |
| 2020/0266798 A1 | 8/2020 | Shelton et al. |
| 2021/0069748 A1 | 3/2021 | Bircumshaw et al. |
| 2021/0078042 A1 | 3/2021 | Bircumshaw et al. |
| 2021/0172788 A1 | 6/2021 | Akkaraju et al. |
| 2021/0236090 A1 | 8/2021 | Akkaraju et al. |
| 2021/0364348 A1 | 11/2021 | Akkaraju et al. |
| 2022/0193722 A1 | 6/2022 | Bircumshaw et al. |
| 2022/0205836 A1 | 6/2022 | Akkaraju et al. |

FOREIGN PATENT DOCUMENTS

| | | |
|---|---|---|
| CN | 103251425 A | 8/2013 |
| CN | 104271266 A | 1/2015 |
| CN | 105310718 A | 2/2016 |
| CN | 106500824 A | 3/2017 |
| CN | 106999163 A | 8/2017 |
| EP | 3453056 A1 | 3/2019 |
| JP | S61223683 A | 10/1986 |
| JP | S6276392 A | 4/1987 |
| JP | H02218983 A | 8/1990 |
| JP | H06350155 A | 12/1994 |
| JP | 2007088805 A | 4/2007 |
| JP | 2007510324 A | 4/2007 |
| JP | 2009165212 A | 7/2009 |
| JP | 2012129662 A | 7/2012 |
| JP | 2013123150 A | 6/2013 |
| JP | 2014000122 A | 1/2014 |
| JP | 2014127921 A | 7/2014 |
| JP | 2015154480 A | 8/2015 |
| JP | 2016503312 A | 2/2016 |
| JP | 2018046512 A | 3/2018 |
| WO | WO-2006123300 A2 | 11/2006 |
| WO | WO-2007099696 A1 | 9/2007 |
| WO | WO-2011026187 A1 | 3/2011 |
| WO | WO-2011033887 A1 | 3/2011 |
| WO | WO-2012117996 A1 | 9/2012 |
| WO | WO-2013043906 A1 | 3/2013 |
| WO | WO-2013158348 A1 | 10/2013 |
| WO | WO-2015131083 A1 | 9/2015 |
| WO | WO-2017025438 A1 | 2/2017 |
| WO | WO-2017132517 A1 | 8/2017 |
| WO | WO-2017182344 A1 | 10/2017 |
| WO | WO-2017216139 A1 | 12/2017 |
| WO | WO-2018102223 A1 | 6/2018 |
| WO | WO-2019164721 A1 | 8/2019 |
| WO | WO-2019199397 A1 | 10/2019 |
| WO | WO-2019199398 A1 | 10/2019 |
| WO | WO-2019226547 A1 | 11/2019 |
| WO | WO-2020028580 A1 | 2/2020 |
| WO | WO-2021050853 A1 | 3/2021 |

OTHER PUBLICATIONS

Co-pending U.S. Appl. No. 17/215,776, inventors Bircumshaw; Brian et al., filed Mar. 29, 2021.

Co-pending U.S. Appl. No. 17/218,656, inventors Kwon; Haesung et al., filed Mar. 31, 2021.

(56) References Cited

OTHER PUBLICATIONS

Co-pending U.S. Appl. No. 17/364,381, inventors Mantravadi; Naresh et al., filed Jun. 30, 2021.
Co-pending U.S. Appl. No. 17/364,397, inventors Kwon; Haesung et al., filed Jun. 30, 2021.
Hill et al. The Role Radius of Curvature Plays in Thiolated Oligonucleotide Loading on Gold Nanopartictes. ACS Nano 3(2):418-424 (2009) Retrieved on Sep. 2, 2021 from https://www.ncbi.nlm.nih.gov/pmc/articles/PMC3241534.
PCT/US2021/024667 International Search Report and Written Opinion dated Jul. 8, 2021.
PCT/US2021/025109 International Search Report and Written Opinion dated Jul. 7, 2021.
PCT/US2021/039977 International Search Report and Written Opinion dated Oct. 6, 2021.
PCT/US2021/039994 International Search Report and Written Opinion dated Nov. 5, 2021.
Zhang et al. Double-SOI wafer-bonded CMUTs with improved electrical safety and minimal roughness of dielectric and electrode surfaces. Journal of microelectromechanical systems 21(3):668-680 (2012).
APC International, Ceramic manufacturing series—poling PZT ceramics. https://www.americanpiezo.com/blog/ceramic-manufacturing-series-poling-pzt-ceramics/ [1-3] (2016).
Assef et al., A reconfigurable arbitrary waveform generator using PWM modulation for ultrasound research. BioMedical Engineering OnLine 12:24 [1-13] (2013).
Choudhry et al., Comparison of tissue harmonic imaging with conventional US in abdominal disease. RadioGraphics: Imaging and Therapeutic Technology 20:1127-1135 (2000).
Dahl, Ultrasound beamforming and image formation. http://people.duke.edu/-jjd/RSNA_USbeamforming.pdf [Slide presentation] (c. 2005).
Dausch et al., Theory and operation of 2-D array piezoelectric micromachined ultrasound transducers. IEEE Transactions on Ultrasonics, Ferroelectrics, and Frequency Control 55(11):2484-2492 (2008).
Doerry, Generating nonlinear FM chirp waveforms for radar. Sandia Report, SAND2006-5856:1-34 (2006).
Felix et al., Biplane ultrasound arrays with integrated multiplexing solution for enhanced diagnostic accuracy in endorectal and transvaginal imaging. http://www.vermon.com/vermon/publications/Felix_UFFC_2005.pdf (2005).
Goldman, Apple's Lightning connector and you: what you should know. CNET Sep. 19, 2012: https://www.cnet.com/news/apples-lightning-connector-and-you-what-you-should-know/ (2012).
Guedes et al., Aluminum nitride pMUT based on a flexurally-suspended membrane. IEEE 16th International Solid-State Sensors, Actuators and Microsystems Conference:12169346 (2011).
Hajati et al. Three-dimensional micro electromechanical system piezoelectric ultrasound transducer. Appl. Phys. Lett. 101:253101 (2012); doi: 10.1063/1.4772469 (2012).
Harput, Use of chirps in medical ultrasound imaging. Ultrasound Group, School of Electronic and Electrical Engineering, University of Leeds, PHD Thesis, Dec. 2012.
Karki, Signal conditioning piezoelectric sensors. Texas Instruments Application report, SLA033A:1-5 (2000).
Khuri-Yakub et al., Capacitive micro machined ultrasonic transducers for medical imaging and therapy. Journal of Micromech Microeng. 21(5):054004-054014 (2011).
Lach et al., Piezoelectric materials for ultrasonic probes. http://www.ndt.net/article/platte2/platte2.htm NDTnet 1(9):1-9 (1996).
Lee et al., Wafer-to-wafer alignment for three-dimensional integration: a review. Journal of MicroElectroMechanical Systems 20(4):885-898 (2011).
Lu et al., High frequency piezoelectric micromachined ultrasonic transducer array for intravascular ultrasound imaging. Proceedings of the IEEE International Conference on Micro Electro Mechanical Systems (MEMS):06765748 (2014).
Martin, Introduction to B-mode imaging. Cambridge University Press; Diagnostic Ultrasound: Physics and equipment, 2nd Edition. Chapter 1:1-10 (2010).
Mina, High frequency transducers from PZT films. Materials Science and Engineering Thesis; Pennsylvania State University: 1-199 (2007).
Moazzami et al., Electrical characteristics of ferroelectric PZT thin films for DRAM applications. IEEE Transaction on Electron Devices 39(9):2044-2049 (1992).
Orenstein Scanning in pain—sonographers seek relief from job-related hazard. Radiology Today 10(8):24 (2009).
Ovland, Coherent plane-wave compounding in medical ultrasound imaging. NTNU—Trondheim, Norwegian University of Science and Technology, Master of Science Thesis, 1-62 (Jun. 2012).
PCT/US2017/063163 International Search Report and Written Opinion dated Feb. 15, 2018.
PCT/US2019/021501 International Search Report and Written Opinion dated Jul. 12, 2019.
PCT/US2019/021515 International Search Report and Written Opinion dated May 31, 2019.
PCT/US2019/033119 International Search Report and Written Opinion dated Aug. 9, 2019.
PCT/US2019/044528 International Search Report and Written Opinion dated Oct. 16, 2019.
PCT/US2020/050374 International Search Report and Written Opinion dated Feb. 2, 2021.
PCT/US2020/050374 Invitation to Pay Additional Fees dated Nov. 13, 2020.
Pye et al., Adaptive time gain compensation for ultrasonic imaging. Ultrasound in Medicine and Biology 18(2):205-212 [abstract] (1992).
Rodriguez et al., Low cost matching network for ultrasonic transducers. Physics Procedia 3:1025-1031 (2010).
Smyth, Design and modeling of a PZT thin film based piezoelectric micromachined ultrasonic transducer (PMUT). MSME Thesis, MIT:1-156 (2012).
Spectral doppler. http://www.echocardiographer.org/Echo%20Physics/spectral%20doppler.html (2017).
Szabo. Diagnostic ultrasound imaging: inside out. Elsevier Academic Press, ISBN: 0-12-680145-2 (572 pgs) (2014).
Trots et al., Synthetic aperture method in ultrasound imaging. InTech Press; Ultrasound Imaging, Masayuki Tanabe (Ed.). http://www.intechopen.com/books/ultrasound-imaging/synthetic-aperture-method-in-ultrasound-imaging. Chapter 3:37-56 (2011).
U.S. Appl. No. 15/820,319 Office Action dated May 14, 2020.
U.S. Appl. No. 15/951,118 Office Action dated Sep. 20, 2019.
U.S. Serial No. 15/951, 121 Office Action dated May 6, 2019.
U.S. Serial No. 15/951, 121 Office Action dated Nov. 19, 2019.
U.S. Appl. No. 16/833,333 Office Action dated Sep. 8, 2020.
Wang et al., Broadband piezoelectric micromachined ultrasonic transducer (pMUT) using mode-merged design. Proceedings of the 10th IEEE International Conference on Nano/Micro Engineered and Molecular Systems (IEEE-NEMS 2015):15260900. Xi'an, China, Apr. 7-11, 2015.
Wang et al., Zero-bending piezoelectric micromachined ultrasonic transducer (pMUT) with enhanced transmitting performance. Journal of Microelectromechanical Systems 24(6):2083-2091 (2015).
U.S. Appl. No. 16/837,800 Office Action dated May 7, 2021.

* cited by examiner

SYSTEMS AND METHODS FOR INTEGRATING ULTRASONIC TRANSDUCERS WITH HYBRID CONTACTS

CROSS-REFERENCE TO RELATED APPLICATIONS

This application is a continuation of International Patent Application No. PCT/US2019/044528, filed Jul. 31, 2019, which claims the benefit of U.S. Provisional Application No. 62/713,272, filed Aug. 1, 2018, which is hereby incorporated by reference in its entirety.

BACKGROUND

An ultrasound transducer commonly includes a diaphragm, a substrate which forms a backing of the diaphragm, and contact(s) that connects the diaphragm to enable signal communication to and from the transducer.

Micromachined ultrasonic transducer (MUT) array(s) offer immense opportunity in the field of ultrasonics due to their efficiency in transducing between the electrical and acoustic energy domains.

SUMMARY

A MUT chip integrated with a circuit, e.g., Application-specific integrated circuit (ASIC), features electrical contact(s) that is configured to transmit and receive signals to and from the MUT and ASIC. In addition, the electrical contact(s) can play a secondary but significant role in dictating the MUT dynamics because they act as a mechanical spring that impacts critical boundary conditions (e.g., mechanical boundary conditions such as how the MUT is attached to the MUT array, how the MUT array is anchored to the ASIC, and how the MUT is connected to the transmission media) of the MUT. As such, an integrated MUT with ASIC using only electrical contacts may destabilize the MUT and reduce dynamic performance of the MUTs.

The present disclosure includes systems and methods that enable MUT integration to an ASIC via hybrid contacts. A hybrid contact herein can enable both electrical connection as well as non-electrical connection, e.g., mechanical connection for the purpose of enhancing MUT dynamics, for example, magnitude of pressure output, surface velocity, and ultrasonic frequency bandwidth of the MUTs. The systems and methods herein can significantly enhance dynamic performance of MUTs. Such systems and methods may utilize one or more of: (1) adding additional mechanical contacts to the MUT, (2) arranging the contacts (electrical and/or mechanical), and (3) modifying the dimensions and shape of the contacts (electrical and/or mechanical).

In one aspect, disclosed herein are ultrasonic transducer systems with hybrid contacts comprising: an ultrasonic transducer element comprising a substrate and a membrane; an electrical circuitry; and one or more contacts connected to the ultrasonic transducer element and the electrical circuitry, wherein the one or more contacts are: designed geometrically using a set of rules; arranged with respect to the membrane based on the set of rules or a second set of rules, or both. In some embodiments, the ultrasonic transducer element is a micromachined ultrasonic transducer (MUT) element. In some embodiments, the ultrasonic transducer element is a piezoelectric micromachined ultrasonic transducer (pMUT) element. In some embodiments, the ultrasonic transducer system further comprises: a second ultrasonic transducer element comprising a second substrate and a second membrane; a second electrical circuitry; and one or more additional contacts connected to the second ultrasonic transducer element and the second electrical circuitry, wherein the one or more additional contacts optionally designed geometrically using the set of rules, and wherein the one or more additional contacts are arranged with respect to the second membrane based on the set of rules or the second set of rules. In some embodiments, the first and the second ultrasonic transducer elements form an array with a plurality of additional ultrasonic transducer elements. In some embodiments, the array is two-dimensional. In some embodiments, the array is 32 by 32, 32 by 64, 32 by 194, 12 by 128, 24 by 128, 32 by 128, 64 by 128, 64 by 32, or 64 by 194. In some embodiments, the electric circuitry is an application specific integrated circuit (ASIC). In some embodiments, the one or more contacts comprise at least one contact that is not hybrid contact. In some embodiments, the one or more contacts are electrical contacts only or mechanical contacts only. In some embodiments, the one or more contacts are hybrid contacts. In some embodiments, the one or more contacts comprise at least one electrical contact and one mechanical contact. In some embodiments, the one or more contacts comprise at least one contact that is both electrical and mechanical. In some embodiments, the set of rules comprises one or more of: a range of diameter, a range of height, a range of aspect ratio, and one or more shapes of the one or more contacts. In some embodiments, the range of diameter is about 5 μm to about 100 μm. In some embodiments, the range of height is about 0 μm to about 300 μm. In some embodiments, the aspect ratio of height to effective diameter is less than about 60:1. In some embodiments, the one or more shapes are from: a cylinder, an annular shape, a cubic shape, a cuboid shape, and an elongated shape. In some embodiments, the second set of rules comprises one or more of: a range of spacing of the one or more contacts to the membrane, a minimum number of electrical contacts within the ultrasonic transducer element, a maximum number of electrical contacts within the ultrasonic transducer element, a minimum number of mechanical contacts within the ultrasonic transducer element, a maximum number of mechanical contacts within the ultrasonic transducer element, a minimum number of hybrid contacts within the ultrasonic transducer element, a maximum number of hybrid contacts within the ultrasonic transducer element. In some embodiments, the range of spacing is no less than about 5 μm. The ultrasonic transducer system of claim 19, wherein the minimum number of electrical contacts is 2. In some embodiments, the maximum number of electrical contacts is 4. In some embodiments, the minimum number of mechanical contacts is 2. In some embodiments, the minimum number of mechanical contacts is a single contact. In some embodiments, the maximum number of mechanical contacts is 10. In some embodiments, the second set of rules comprises: arranging the one or more contacts to be symmetrical about an axis of the membrane; and arranging the one or more contacts to surround the membrane, or their combination.

In another aspect, disclosed herein are methods of improving performance of an ultrasonic transducer system using hybrid contacts, comprising: obtaining an ultrasonic transducer system, the ultrasonic transducer system comprising: an ultrasonic transducer element comprising a substrate and a membrane; and an electrical circuitry connected to the ultrasonic transducer element; obtaining one or more contacts, the one or more contacts optionally designed geometrically using a set of rules; adding the one or more contacts to the ultrasonic transducer element, comprising:

arranging the one or more contacts with respect to the membrane based on the set of rules or a second set of rules; and connecting the one or more contacts to the ultrasonic transducer element and the electrical circuitry.

In yet another aspect, disclosed herein are methods of improving performance of an ultrasonic transducer system using hybrid contacts, comprising: obtaining an ultrasonic transducer system, the ultrasonic transducer system comprising: an ultrasonic transducer element comprising a substrate and a membrane; and an electrical circuitry connected to the ultrasonic transducer element; obtaining one or more contacts, the one or more contacts optionally designed geometrically using a set of rules; adding the one or more contacts to the ultrasonic transducer system, comprising: arranging the one or more contacts with respect to the membrane based on the set of rules or a second set of rules; and connecting the one or more contacts to the ultrasonic transducer element and the electrical circuitry. In some embodiments, the ultrasonic transducer element is a micromachined ultrasonic transducer (MUT) element. In some embodiments, the ultrasonic transducer element is a piezoelectric micromachined ultrasonic transducer (pMUT) element. In some embodiments, the ultrasonic transducer system further comprise: a second ultrasonic transducer element comprising a second substrate and a second membrane; a second electrical circuitry; and one or more additional contacts connected to the second ultrasonic transducer element and the second electrical circuitry, wherein the one or more additional contacts optionally designed geometrically using the set of rules, and wherein the one or more additional contacts are arranged with respect to the second membrane based on the set of rules or the second set of rules. In some embodiments, the first and the second ultrasonic transducer elements form an array with a plurality of additional ultrasonic transducer elements. In some embodiments, the array is two-dimensional. In some embodiments, the array is 32 by 32, 32 by 64, 32 by 194, 12 by 128, 24 by 128, 32 by 128, 64 by 128, 64 by 32, or 64 by 194. In some embodiments, the electric circuitry is ASIC. In some embodiments, the one or more contacts comprise at least one contact that is not a hybrid contact. The method can be performed with one or more contacts being electrical contacts only or mechanical contacts only. In some embodiments, the one or more contacts are hybrid contacts. In some embodiments, the one or more contacts comprise at least one electrical contact and one mechanical contact. In some embodiments, the one or more contacts comprise at least one contact that is both electrical and mechanical. In some embodiments, the set of rules comprises one or more of: a range of diameter, a range of height, a range of aspect ratio, and a shape of the one or more contacts. In some embodiments, the range of diameter is about 5 µm to about 100 µm. In some embodiments, the range of height is about 0 µm to about 300 µm. In some embodiments, the aspect ratio is less than about 60:1. In some embodiments, the shape is one or more selected from: a cylinder, an annular shape, and an elongated shape. In some embodiments, the second set of rules comprises one or more of: a range of spacing of the one or more contacts to the membrane, a minimum number of electrical contacts within the ultrasonic transducer element, a maximum number of electrical contacts within the ultrasonic transducer element, a minimum number of mechanical contacts within the ultrasonic transducer element, a maximum number of mechanical contacts within the ultrasonic transducer element, a minimum number of hybrid contacts within the ultrasonic transducer element, a maximum number of hybrid contacts within the ultrasonic transducer element. In some embodiments, the range of spacing is no less than about 5 µm. In some embodiments, the minimum number of electrical contacts is 2. In some embodiments, the maximum number of electrical contacts is 4. In some embodiments, the minimum number of mechanical contacts is 2. In some embodiments, the minimum number of mechanical contacts is a single contact. In some embodiments, the maximum number of mechanical contacts is 10. In some embodiments, the second set of rules comprises: arranging the one or more contacts to be symmetrical about an axis of the membrane; arranging the one or more contacts to surround the membrane, or their combination.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

DETAILED DESCRIPTION

Figure 1A:
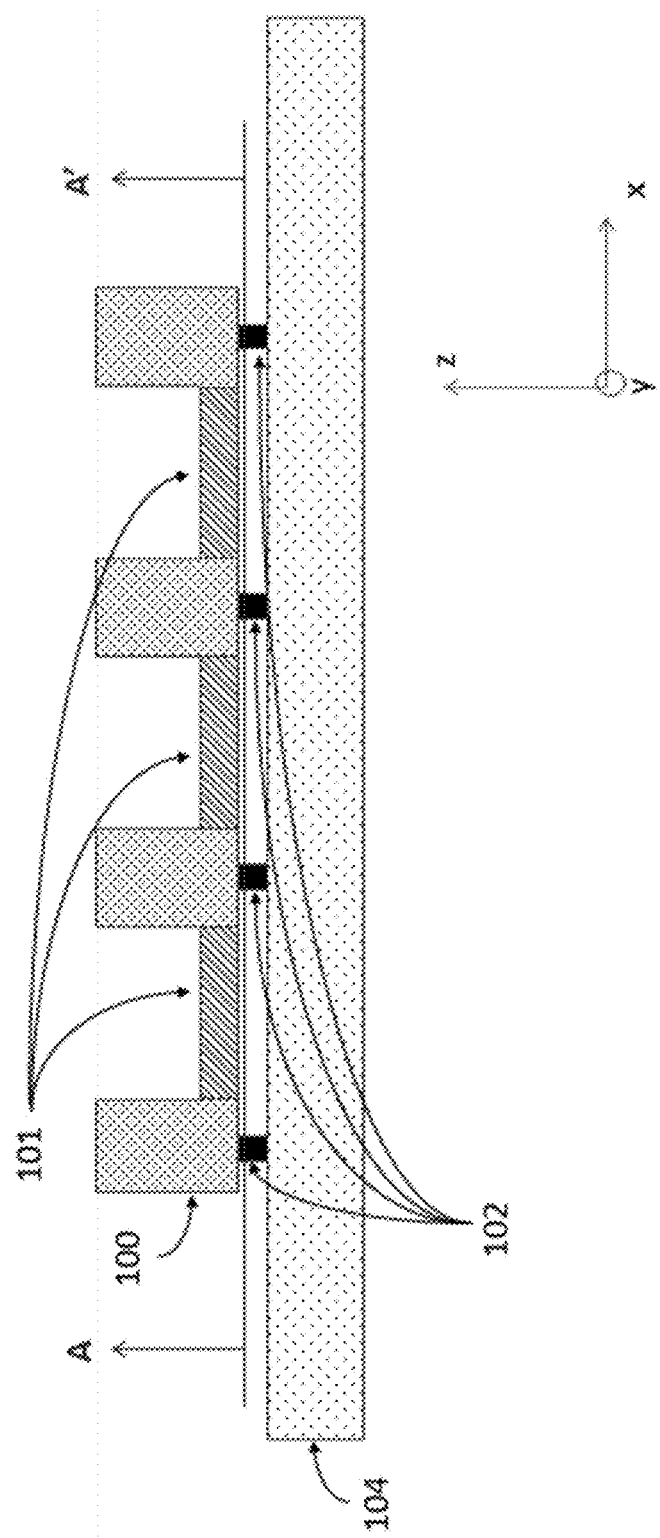
FIGS. 1A-1B show a cross-section view and layout view, respectively, of an exemplary embodiment of an integrated MUT and ASIC system using electrical contacts with asymmetry in the electrical contacts (102) (the ASIC die (104) is removed from this figure for clarity purposes)

In some embodiments, a transducer herein is a device that converts a physical variation in one energy domain into a physical variation in a different domain. A micromachined ultrasonic transducer (MUT), for example, converts electrical variations into mechanical vibrations of a diaphragm. These vibrations of the diaphragm result in pressure waves in any gas, liquid, or solid adjoining the diaphragm. Conversely, pressure waves in the adjoining media may cause mechanical vibration of the diaphragm. The diaphragm vibration may in turn result in electrical variations on the MUT's electrodes, which can be sensed. For a piezoelectric MUT (pMUT), an electrical field across the piezoelectric film will change the strain on the diaphragm which may cause the diaphragm to move and subsequently generate pressure waves. Impinging pressure waves from the media onto the pMUT may, in turn, vibrate the diaphragm and create strain in the piezoelectric film which may produce a change in charge on the electrodes of the pMUT.

In certain embodiments, disclosed herein are electrical transducers in which one of the two energy domains is electrical. In some embodiments, disclosed herein are ultrasonic transducers that are electrical transducers. For example, the pMUT (piezoelectric MUT) is an electrical transducer as the electrical domain is one of the energy domains the pMUT converts between while the other domain being mechanical, e.g., mechanical pressure.

The present disclosure includes methods of changing the dynamic behavior of an electrical transducer. In some embodiments, the methods herein are applicable to electrical transducers, ultrasonic transducers, MUT transducers, pMUT transducers, or any other types of transducers. In some embodiments, the methods herein are applicable to electrical transducers other than pMUT, including but not limited to capacitive, piezo-resistive, thermal, optical, radioactive transducers. A piezo-resistive pressure transducer, for example, converts mechanical pressure variations into changes in electrical resistance variations via the piezoresistance effect. Because the resistance variations are in the electrical domain, the piezo-resistive pressure transducer qualifies as an electrical transducer.

Certain Definitions

Unless otherwise defined, all technical terms used herein have the same meaning as commonly understood by one of ordinary skill in the art to which this invention belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 10%, 5%, or 1%, including increments therein.

The systems and methods herein include a MUT integrated with an ASIC featuring both electrical contacts to transmit/receive signals to/from the ASIC as well as non-electrical contacts (e.g., mechanical contacts) to ensure dynamic performance and reliability of the MUT. In some embodiments, unlike contact arrangements in conventional chip designs, the contacts can be located close to the mechanically sensitive membrane portion of the MUTs, where the membrane vibrates at high frequency band of about 1 MHz to about 10 MHz. As a result, the contact design (e.g., contact type, location, shape, size, etc) can be very important in order to ensure dynamic performance and reliability of the MUT. In some embodiments, the systems and methods herein includes arranging the contacts in such a way to enhance mechanical performance of a MUT (e.g., surface velocity of membrane, magnitude of pressure output, and ultrasonic frequency bandwidth of the MUTs), rather than simply satisfying electrical connectivity and thermal cycle reliability.

In some embodiments, the contact herein connects the elements to which it is attached. In some embodiments, such connection provided by the contact is electrical or non-electrical. In some embodiments, such connection is mechanical. In some embodiments, such connection is mechanical only. In some embodiments, a contact herein is mechanical, although based off its location, the contact may or may not affect the transducer's mechanical operation at a same level. In some embodiments, the contact herein is hybrid, e.g., both electrical and non-electrical. In some embodiments, such hybrid contact herein enables mechanical and electrical contact. In some embodiments, the mechanical contact can be used to carry electrical signals as the electrical contacts, thus making it a hybrid contact. In some embodiments, the hybrid contact may be configured to provide more than one type of connections either simultaneously, or at different time points. For example, a contact may be configured to provide mechanical and electrical connection simultaneously while another contact may be configured to provide electrical connecting but not mechanical connection when a predetermined threshold condition has been met (e.g., a location threshold).

In some embodiments, a hybrid contact array includes more than one type of contacts arranged in one, two, or three dimensions. In some embodiments, a hybrid contact array includes one or more hybrid contacts arranged in one, two, or three dimensions. In some embodiments, the contact herein is a hybrid contact providing any two different type of connections (e.g., electrical and mechanical). In some embodiments, the contact herein is an electrical only (e.g., with no or minimal mechanical effect to the transducer's mechanical operations) and/or mechanical only contact.

In conventional integrated system of MUT and a circuit, e.g., ASIC, the electrical contacts are generally of simple shapes, typically an approximate cylinder shape with a set diameter and height. In conventional integrated system of MUT and ASIC, the position of electrical contacts on the die is typically dictated by the electrical routing of the MUT and the ASIC. Disadvantages can exist in conventional integrated systems as the electrical contacts are often designed (e.g., size, shape, and position, etc.) to achieve thermal cycle reliability with no consideration for MUT performance.

In some embodiments, the MUT here is a MUT array of MUT transducers (interchangeable herein as transducer elements), each MUT transducer having a substrate, a diaphragm (interchangeable here as "membrane"), and/or a piezoelectric element. In some embodiments, the array is in two dimensions. In a MUT array, each MUT transducer acts as a pixel. In some embodiments, the array size may be variable and customized for various applications. Non-limiting exemplary array sizes are: 32 by 32, 32 by 64, 32 by 194, 12 by 128, 24 by 128, 32 by 128, 64 by 128, 64 by 32, or 64 by 194 (columns by rows, or rows by columns).

In some embodiments, the size of each pixel herein is variable and can be customized for various applications. In some embodiments, each pixel herein includes a width (x-axis) and/or height (z axis) that is in the range of about 10 µm to about 1000 µm or 10 µm to 1000 µm. In some embodiments, each pixel herein includes a width (x-axis) that is in the range of about 20 µm to about 600 µm, about 30 µm to about 500 µm, about 40 to about 400 µm, about 50 to about 300 µm, or about 50 µm to about 250 µm. In some embodiments, each pixel herein includes a height that is in the range of about 10 µm to about 1000 µm, about 20 µm to about 950 µm, about 30 to about 900 µm, about 40 to about 850 µm, or about 50 µm to about 800 µm. In some embodiments, the pixel may be asymmetric or symmetric about x, y, z and/or any other axis in the 3D space. In some embodiments, a pixel is taller in the elevation direction, and narrower in the azimuth direction.

In some embodiments, an electrical contact, a mechanical contact, and/or a hybrid contact herein are in close proximity to one or more membranes. In some embodiments, the maximal or minimal distance from an electrical contact 102 or a hybrid contact 105/106 to a membrane 101 is greater than 0 µm, 1 µm, 2 µm, 3 µm, 4 µm, 5 µm, 6 µm, 7 µm, 8 µm, 9 µm, or 10 µm. In some embodiments, the maximal or minimal distance from an electrical contact or a hybrid contact to a membrane is less than 200 µm, 180 µm, 160 µm, 140 µm, 120 µm, 100 µm, 90 µm, 80 µm, 70 µm, 60 µm, 50 µm, 40 µm, 30 µm, 20 µm, 10 µm or even less, including increments therein. In some embodiments, the maximal or minimal distance from an electrical contact or a hybrid contact to a membrane is in the range of about 10 µm to about 100 µm or 10 µm to 100 µm. In some embodiments, the maximal or minimal distance from an electrical contact or a hybrid contact to a membrane is in the range of about 5 µm to about 150 µm or 5 µm to 150 µm.

Figure 1B:
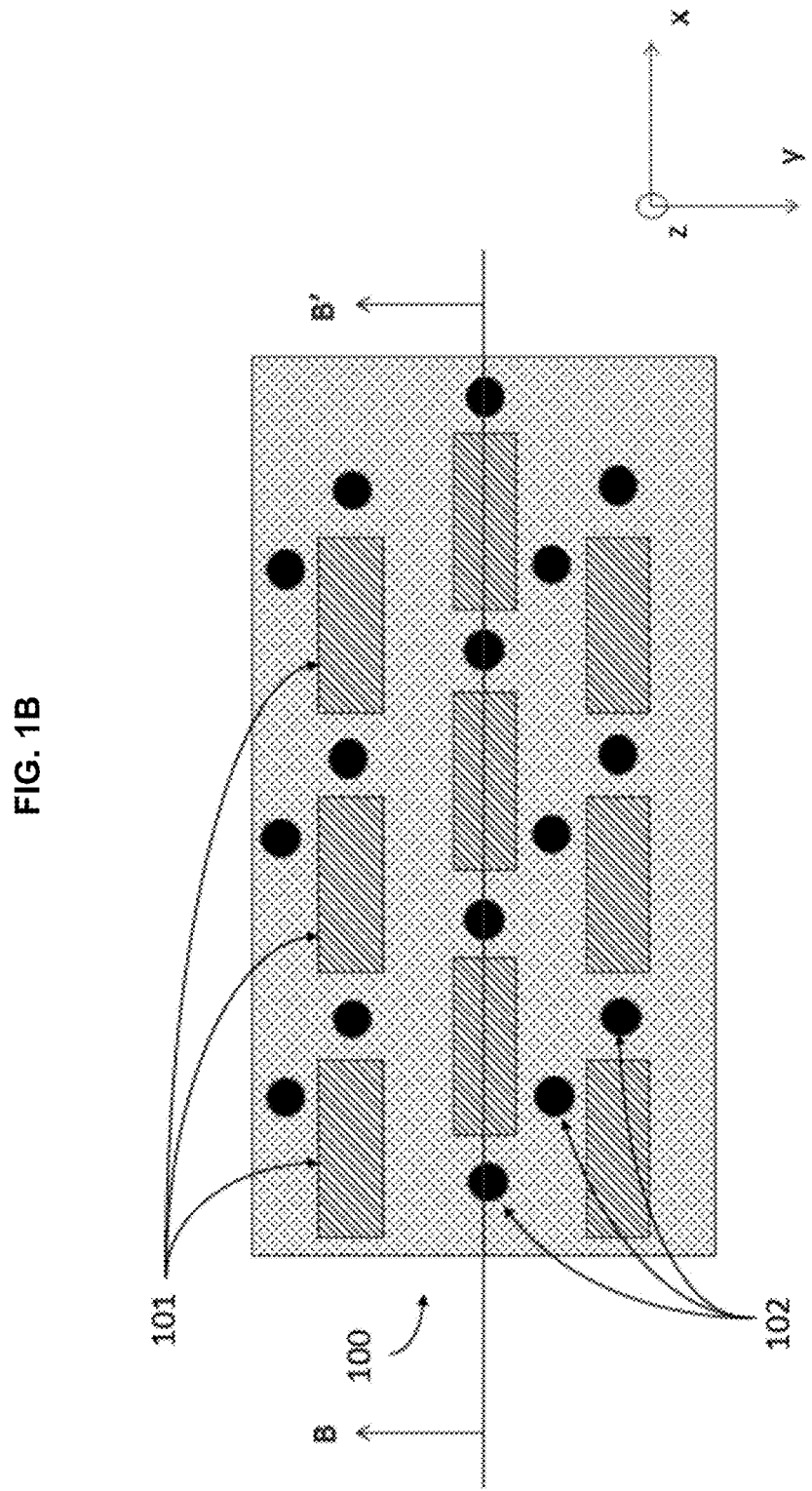

Referring to FIGS. 1A-1B, in a particular embodiment, the integrated system of MUT and ASIC includes a MUT die 100 that is attached or connected to an ASIC die 104 via a plurality of contacts 102. In some embodiments, the ASIC die 104 herein may be other circuit element such as printed circuit board (PCB). The cross-section (at B-B' in FIG. 1B) and layout views (at A-A' in FIG. 1A) of the integrated system are shown in FIGS. 1A and 1B, respectively. In this embodiment, the MUT die includes an array of transducers which includes an array of membranes 101. The arrangement (e.g., number of membranes per row or column, gaps between adjacent membranes, etc) of such membrane array may be variable, and FIG. 1B shows a non-limiting exemplary arrangement of the array. In this embodiment, the contacts are electrical contacts. In some embodiments, the contacts 102 may be configured to provide additional contacts, such as mechanical contacts. In this embodiment, one or more of the electrical contacts 102 are in close proximity (e.g., with a maximal distance in the range of about 10 µm to about 100 µm) to the mechanically sensitive MUT membranes 101. In some embodiments, one or more electrical contacts 102 is configured to form a critical interface between the MUT and ASIC. In some embodiments, one or more electrical contacts 102, and/or mechanical contacts is configured to act as important boundary condition for the MUT dynamics or performance.

Arranging Contacts and/or Adding Additional Contacts

In some embodiments, additional contacts are added to the conventional contact configuration, for example, shown in FIGS. 1A-1B. In some embodiments, each of the added contacts can be an electrical contact, a mechanical contact, or a hybrid contact. In some embodiments, the location of the existing and/or additional contacts (e.g., mechanical contacts) is designed to enhance the thermal stability, structural rigidity and/or dynamic performance of the integrated MUT and ASIC system.

Figure 2:
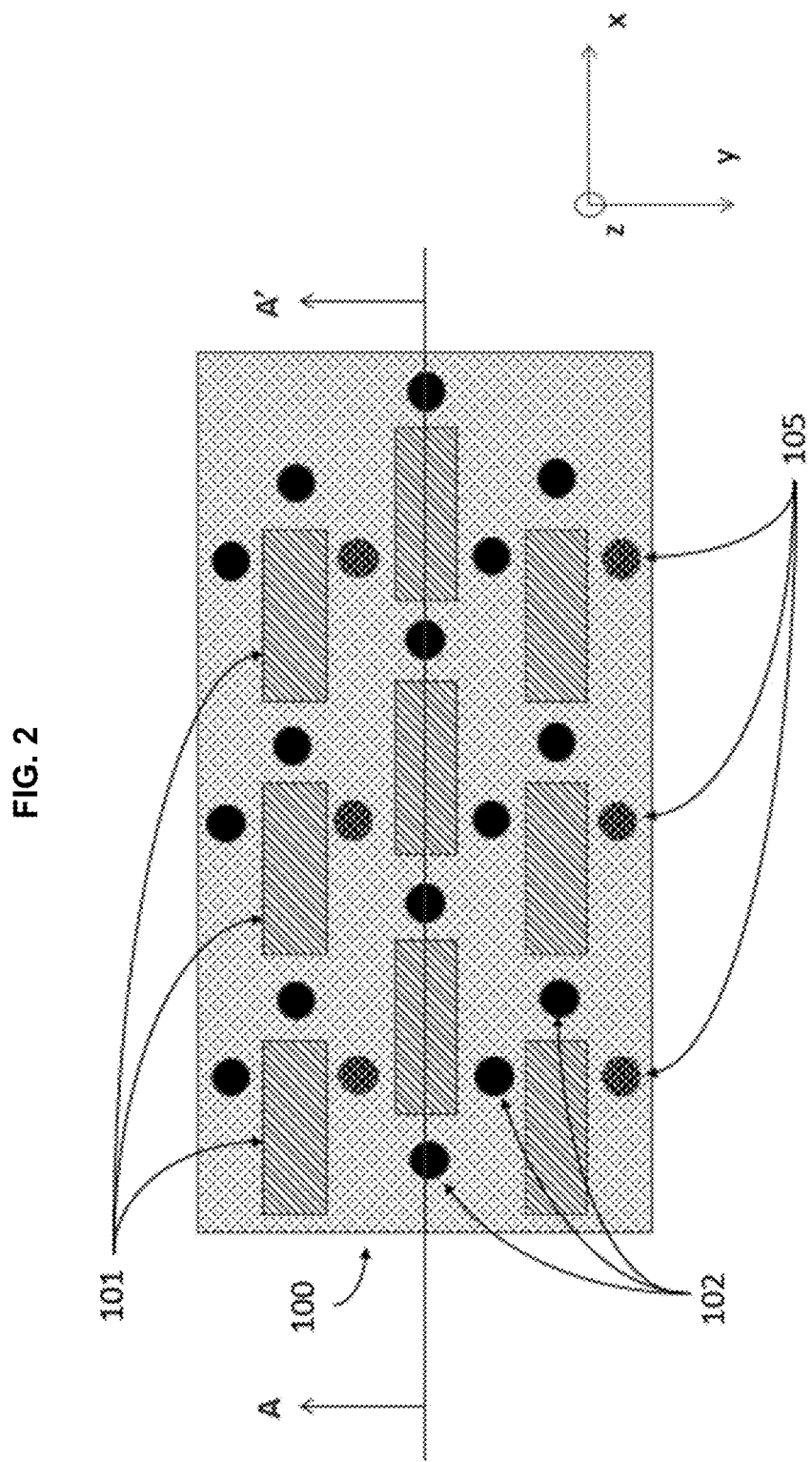
FIG. 2 shows a layout view of an exemplary embodiment of an integrated MUT and ASIC system using hybrid contacts with added contacts for symmetrical boundary conditions.

Referring to FIG. 2, in a particular embodiment, additional contacts are added to the existing asymmetric configuration of contacts shown in FIG. 1B. In this embodiment, the mechanical contacts 105 are added to the conventional electrical contact 102 arrangement and the integrated MUT and ASIC system includes a symmetrical layout of contacts, forming a symmetric array of hybrid contacts, in the x-y plane, optionally about the x axis, y axis, or any other axes within the x-y plane. In some embodiments, a symmetric array includes symmetrical arrangement of identical geometrical shapes of contacts, but the contacts may be of different types, e.g., as shown in FIG. 2. In some embodiments, a symmetric array includes symmetrical arrangement of contacts.

Figure 3:
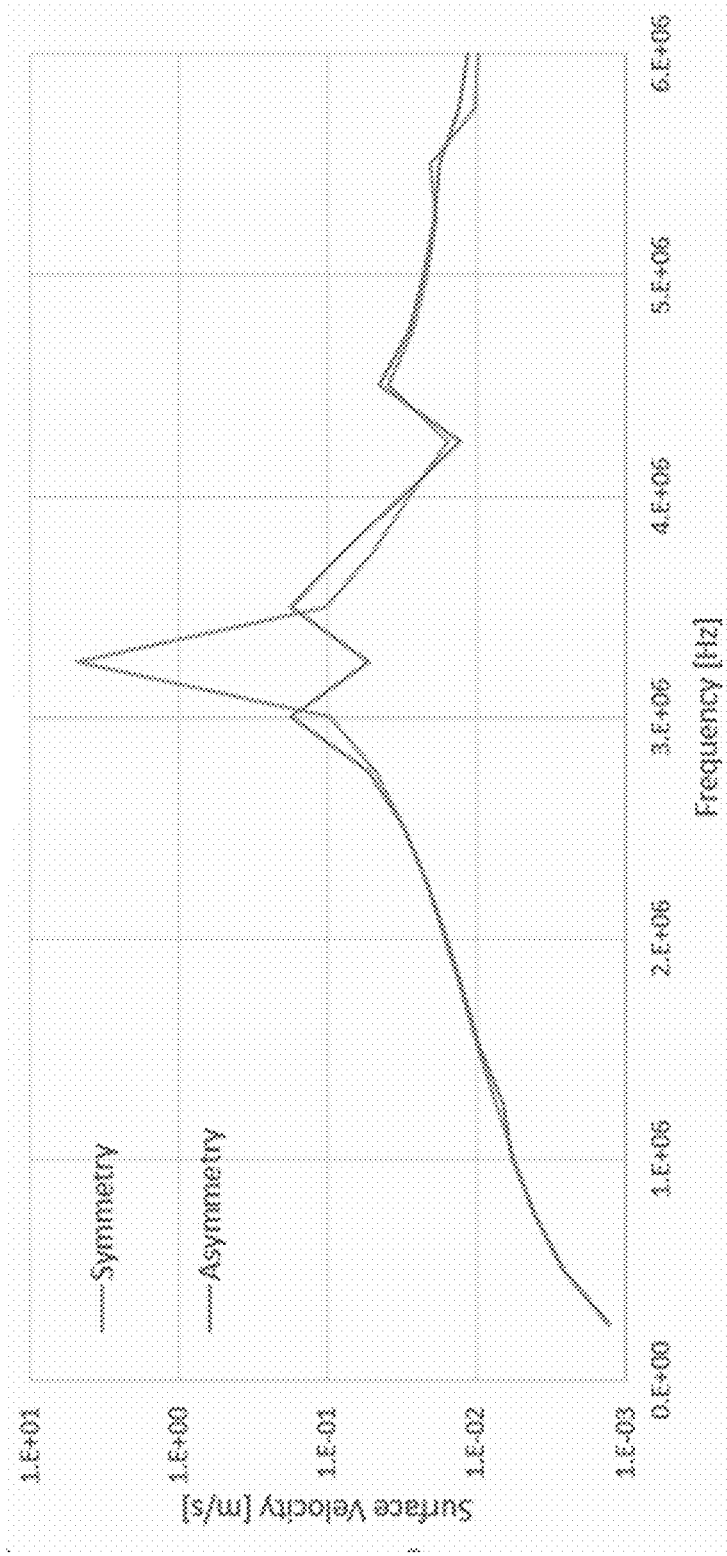
FIG. 3 shows exemplary dynamic response of the central MUT membrane in the MUT array of FIG. 1B with asymmetric contacts and the dynamic response of the central MUT membrane in the MUT array of FIG. 2 with symmetric hybrid contacts.

FIG. 3 shows the surface velocity versus frequency of the asymmetric contact arrangement of FIG. 1B in comparison to the symmetric hybrid contact arrangement of FIG. 2. As can be seen in FIG. 3, the symmetrical contact arrangement in FIG. 2 enables a much higher maximal surface velocity than that of the asymmetrical contact arrangement in FIG. 1B. In some embodiments, an advantage of a MUT is that it is configurable to provide a maximum surface velocity of the membrane higher than other types of ultrasound transducers. In some embodiments, the maximum surface velocity of the membrane is directly related to the maximum pressure output achievable with the MUT. Thus, it is advantageous and highly desirable to provide a higher maximum surface velocity with MUT. Referring to FIG. 3, the symmetric hybrid contact arrangement/array in FIG. 2 can achieve more than an order of magnitude higher maximum surface velocity of the membrane. In the same embodiment shown in FIG. 2, the mechanical contacts can offer additional mechanical support that enhances MUT dynamics such as surface velocity of the membrane. For example, the mechanical contact(s) can shift the primary frequency up or down, move harmonic frequencies relative to the primary frequency, thereby affecting the perceived bandwidth of the device. As another example, the contact(s) may increase or decrease the mechanical damping, thus directly affecting the bandwidth of the transducer for its primary and harmonic mode shapes.

In some embodiments, the maximum surface velocity is variable and can dependent on specific applications. In some embodiments, the maximum surface velocity is in the range of about 0.01 m/second to about 100 m/second. In some embodiments, the maximum surface velocity is in the range of about 0.1 m/second to about 10 m/second. In some embodiments, the maximum surface velocity is in the range of about 2 mm/second to about 100 m/second. In some embodiments, the maximum surface velocity is in the range of about 5 mm/second to about 80 m/second. In some embodiments, the maximum surface velocity is in the range of about 5 mm/second to about 60 m/second. In some embodiments, the maximum surface velocity is in the range of about 6 mm/second to about 50 m/second. In some embodiments, the maximum surface velocity is in the range of about 6 mm/second to about 40 m/second. In some embodiments, the maximum surface velocity is in the range of about 6 mm/second to about 30 m/second. In some embodiments, the maximum surface velocity is in the range of about 8 mm/second to about 30 m/second. In some embodiments, the maximum surface velocity is in the range of about 8 mm/second to about 20 m/second. In some embodiments, the maximum surface velocity is in the range of about 8 mm/second to about 15 m/second. In some embodiments, the maximum surface velocity is in the range of about 10 mm/second to about 10 m/second.

In some embodiments, the integrated MUT and ASIC systems herein include a different symmetric hybrid contact array from the one shown in FIG. 2. Such different symmetric hybrid contact array is configured to improve MUT dynamics over conventional contact arrays. In some embodiments, the symmetric hybrid contact array is symmetrical about x-axis, y axis or any other axes within the x-y plane of the MUT die 100. In some embodiments, the symmetric hybrid contact array herein includes contacts that are symmetrically positioned about the x-axis, y-axis or any other axes within the x-y plane of individual MUT membrane 101. In some embodiments, symmetry herein includes: size, shape, type, position, or their combinations of the contact(s). For example, two different contacts (e.g., one hybrid, one electrical) positioned symmetrically about a MUT membrane may be considered a symmetrical arrangement of such two contacts.

In some embodiments, the systems and methods herein includes a MUT array with an arbitrary number of membranes. In some embodiments, the total number of membranes in the MUT array is in the range of 1 to 15,000. In some embodiments, the number of membranes in the MUT array is in the range of 250 to 4,200.

In some embodiments, the systems and methods herein includes a MUT array with an arbitrary number of contacts or hybrid contacts. In some embodiments, the number of contacts or hybrid contacts in the MUT array is in the range of 2 to 120,000. In some embodiments, the number of contacts or hybrid contacts in the MUT array is in the range of 250 to 8,500.

Designing the Hybrid Contacts

Figure 4:
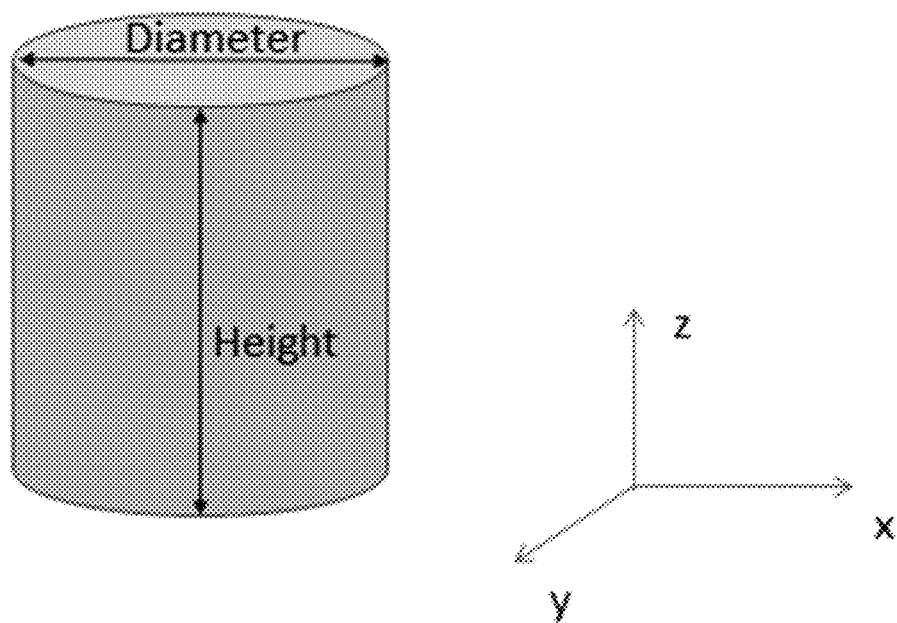
FIG. 4 show exemplary geometrical parameters of a cylindrical electrical and/or mechanical contact of an integrated MUT and ASIC system herein.

In some embodiments, arrangement of the hybrid contacts is not the sole parameter of the systems and methods herein. The contacts themselves can be designed to further optimize MUT performance. Typically, the contact materials can be set by the integration technology, and so are fixed. As noted previously, in the cases where contacts are typically cylindrical, the contact height (along z axis) and diameter (x-y plane) can be parameters for optimization, as shown in FIG. 4.

In some embodiments, MUT performance can be improved or optimized for a given MUT design and integration scheme using a first set of rules, a second set of rules, or their combinations. The first set of rules, for each contact, can include: a range of diameter, a range of height, range of cross section area, a range of aspect ratio, a shape of the one or more contacts, and a cross-section shape of the one or more contacts. The second set of rules, which may provide for each contact one or more of: a range of spacing of the one or more contacts to the membrane, a minimum number of electrical contacts within the ultrasonic transducer element, a maximum number of electrical contacts within the ultrasonic transducer element, a minimum number of mechanical contacts within the ultrasonic transducer element, a maximum number of mechanical contacts within the ultrasonic transducer element, a minimum number of hybrid contacts within the ultrasonic transducer element, a maximum number of hybrid contacts within the ultrasonic transducer element, a maximum contact area with the ultrasonic transducer element, a minimum contact area with the ultrasonic transducer element. Thus, using one or more such rules may help optimize the MUT performance. For example, a contact shape may be given as cylindrical, and the integration scheme may be provided to be via hybrid contact. The other rules of the first and/or the second set of rules can be selected, either manually, empirically, automatically, or using machine learning algorithms to determine features of the contacts thus optimize MUT performance.

Figure 5:
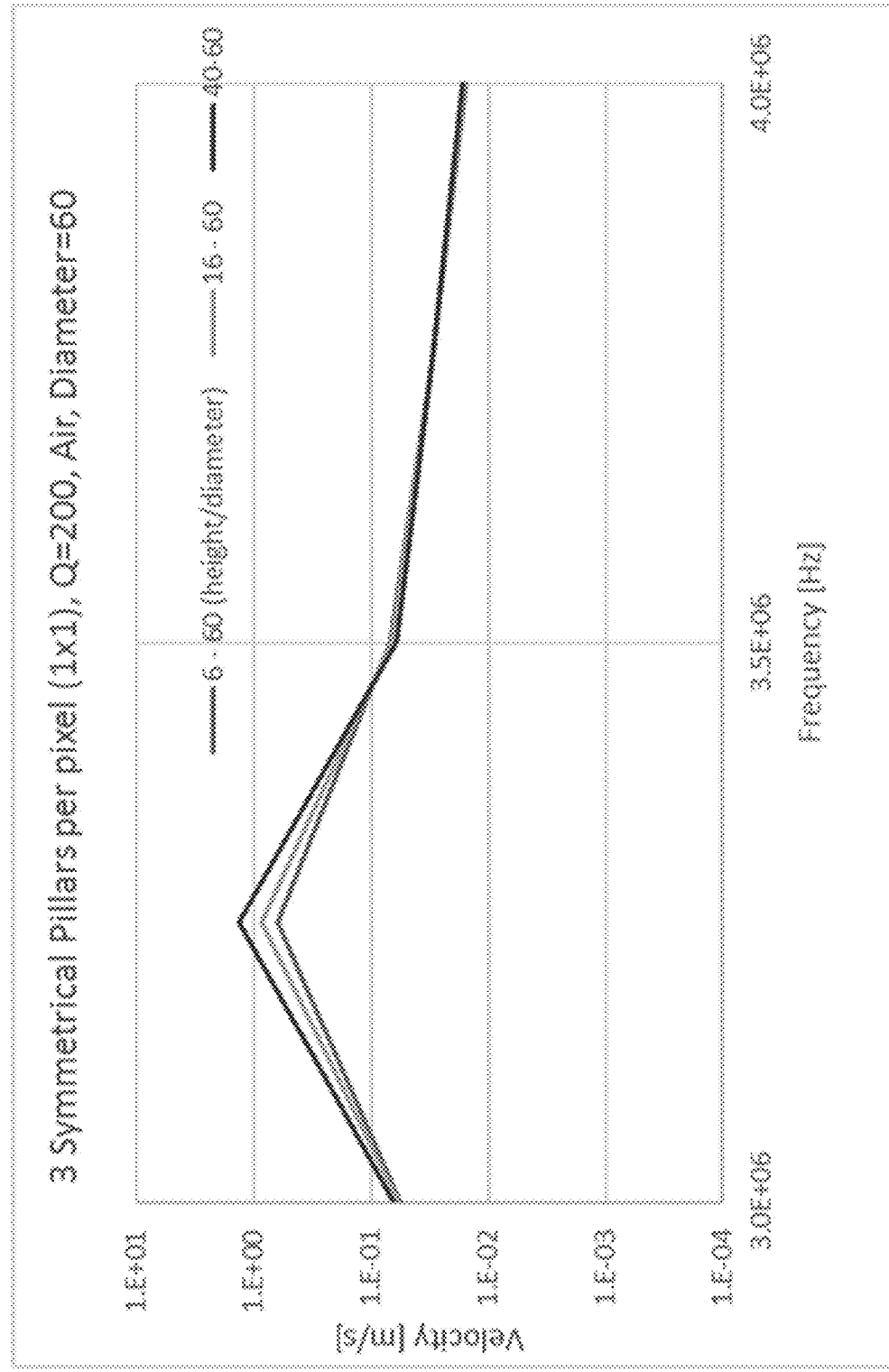
FIG. 5 shows exemplary performance of the integrated MUT and ASIC system with hybrid contact arrangement as shown in FIG. 2 with contacts of a 60 µm diameter and three different heights: 6 µm, 16 µm, and 40 µm.
Figure 6:
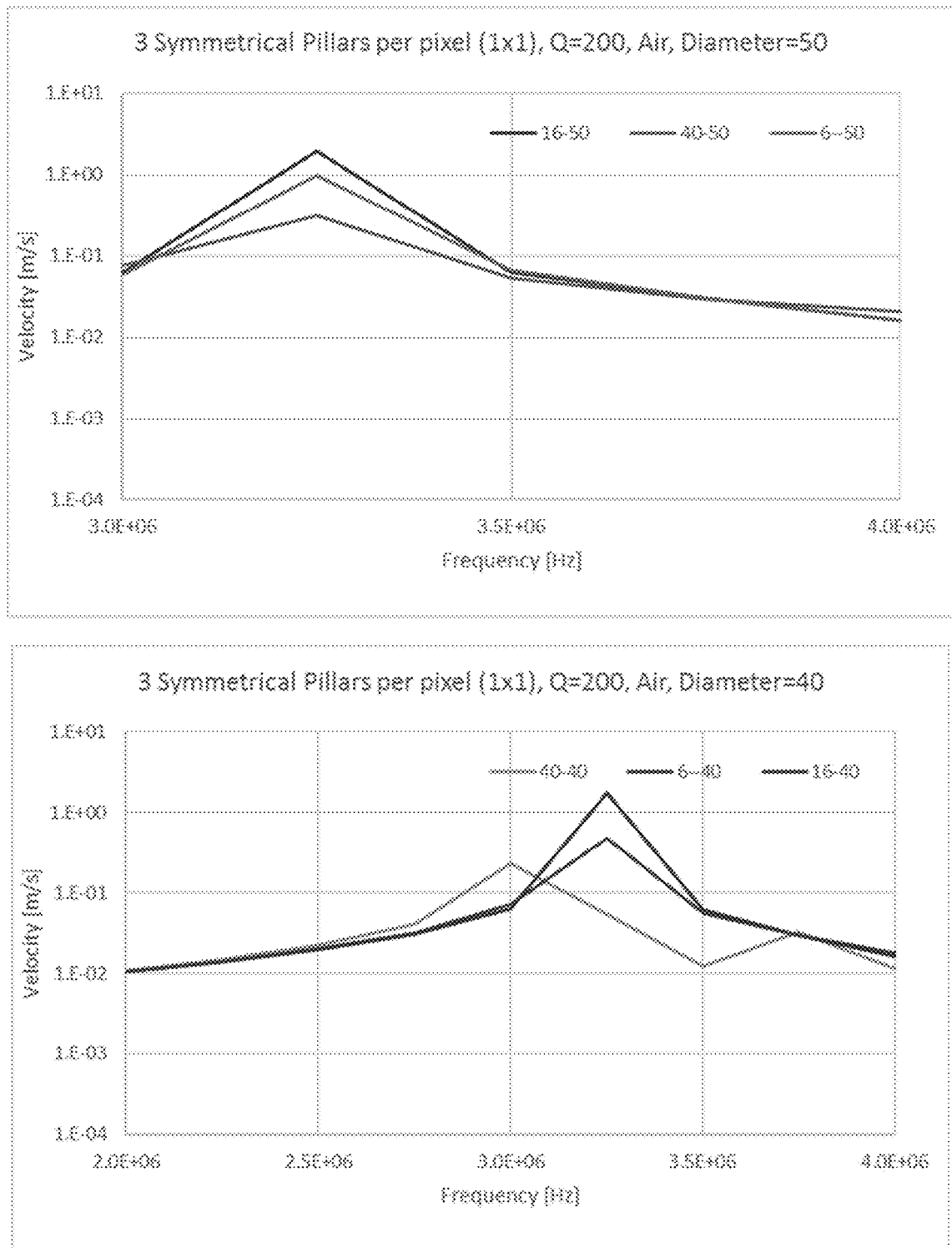
FIG. 6 shows exemplary performance of the integrated MUT and ASIC system with hybrid contact arrangement as shown in FIG. 2 with contacts of a 50 µm diameter (left) and 40 µm diameter (right), at three different heights: 6 µm, 16 µm, and 40 µm.

FIG. 5 shows the dynamic performance of the MUT membrane 101 of the hybrid contact configuration illustrated in FIG. 2. In this particular embodiment, the contact with the tallest height of three different heights, i.e., 40 μm, has the best performance compared to 6 μm and 16 μm high contacts, for an identical contact diameter of 60 μm. If the contact diameter is adjusted to 50 μm, the best contact height is 16 μm as illustrated in FIG. 6 (left). For a contact diameter of 40 μm, the best contact height is 6 μm as in FIG. 6 (right).

In some embodiments, the contacts herein can be of shapes other than cylindrical shapes to achieve optimized MUT performance. Non-limiting examples of three dimensional contact shape includes a part or entirety of: a sphere, pyramid, baseball, spindle shape, cube, cuboid, tetrahedron, cone, hexagonal prism, triangular prism, and donut shape. Non-limiting examples of contact shapes along the x-y plane include a part or entirety of: a circle, ring, fan, oval, triangle, square, rectangular, trapezoid, rhomboid, and polygon.

In some embodiments, the contact herein includes a height (along z axis) that can be variable and customized for different applications. In some embodiments, the contact herein includes a height (along z axis) in the range of about 0 μm to 300 μm. In some embodiments, the contact herein includes a height in the range of about 0 μm to 250 μm. In some embodiments, the contact herein includes a height in the range of about 0 μm to 200 μm. In some embodiments, the contact herein includes a height in the range of about 0 μm to 100 μm. In some embodiments, the contact herein includes a height in the range of about 1 μm to 100 μm. In some embodiments, the contact herein includes a height in the range of about 1 μm to 80 μm. In some embodiments, the contact herein includes a height in the range of about 2 μm to 80 μm. In some embodiments, the contact herein includes a height in the range of about 2 μm to 60 μm. In some embodiments, the contact herein includes a height in the range of about 3 μm to 60 μm. In some embodiments, the contact herein includes a height in the range of about 3 μm to 50 μm.

In some embodiments, the contact herein includes a diameter (in x-y plane) that can be variable and customized for different applications. In some embodiments, the contact herein includes a diameter (in x-y plane) in the range of about 0 μm to 300 μm. In some embodiments, the contact herein includes a diameter in the range of about 0 μm to 250 μm. In some embodiments, the contact herein includes a diameter in the range of about 4 μm to 120 μm. In some embodiments, the contact herein includes a diameter in the range of about 5 μm to 100 μm. In some embodiments, the contact herein includes a diameter in the range of about 10 μm to 90 μm. In some embodiments, the contact herein includes a diameter in the range of about 15 μm to 80 μm. In some embodiments, the contact herein includes a diameter in the range of about 20 μm to 80 μm. In some embodiments, the contact herein includes a diameter in the range of about 25 μm to 75 μm. In some embodiments, the contact herein includes a diameter in the range of about 25 μm to 70 μm. In some embodiments, the contact herein includes a diameter in the range of about 30 μm to 60 μm.

In some embodiments, the contact herein includes an aspect ratio (i.e., height:diameter) (that can be variable and customized for different applications. Non-limiting examples of aspect ratio includes but is not limited to: less than 6:1, less than 5:1, less than 4:1, less than 3:1, or less than 2:1. In some embodiments, the aspect ratio is less than 1:1. In some embodiments, the aspect ratio is less than 0.9:1. In some embodiments, the aspect ratio is less than 0.8:1. In some embodiments, the aspect ratio is less than 0.7:1. In some embodiments, the aspect ratio is less than 0.6:1. In some embodiments, the aspect ratio is less than 0.5:1. In some embodiments, the aspect ratio is less than 0.4:1. In some embodiments, the aspect ratio is less than 0.3:1. In some embodiments, the aspect ratio is less than 1.2:1. In some embodiments, the aspect ratio is less than 0.2:1. In some embodiments, the aspect ratio is less than 0.8:1. In some embodiments, the aspect ratio is less than 1.5:1.

In some embodiments, the contacts herein include a contact area in the x-y plane. In some embodiments, the contact area contacts the transducer element and/or the circuit herein. In some embodiments, the contact area is a cross section perpendicular to the z-axis. In some embodiments, the contact area is equivalent to a circle of diameter ranging from 30 μm to 60 μm.

In some embodiments, the contact area is equivalent to a circle of diameter ranging from 10 μm to 100 μm. In some embodiments, the contact area is equivalent to a circle of diameter ranging from 20 μm to 80 μm. In some embodiments, the contact area is equivalent to a circle of diameter ranging from 30 μm to 50 μm. In some embodiments, the contact area is equivalent to a circle of diameter ranging from 40 μm to 60 μm.

In some embodiments, each pixel herein includes one or more electrical, mechanical, and/or hybrid contacts. In some embodiments, each pixel includes 1 to 5, 1 to 4, 1 to 3, or 1 to 2 electrical contacts. In some embodiments, each pixel includes 1 to 10, 1 to 8, 1 to 6, or 1 to 5, 1 to 4, 1 to 3, or 1 to 2 mechanical contacts. In some embodiments, each pixel includes 1 to 10, 1 to 8, 1 to 6, or 1 to 5, 1 to 4, 1 to 3, or 1 to 2 hybrid contacts.

Shaping Hybrid Contacts

Figure 7:
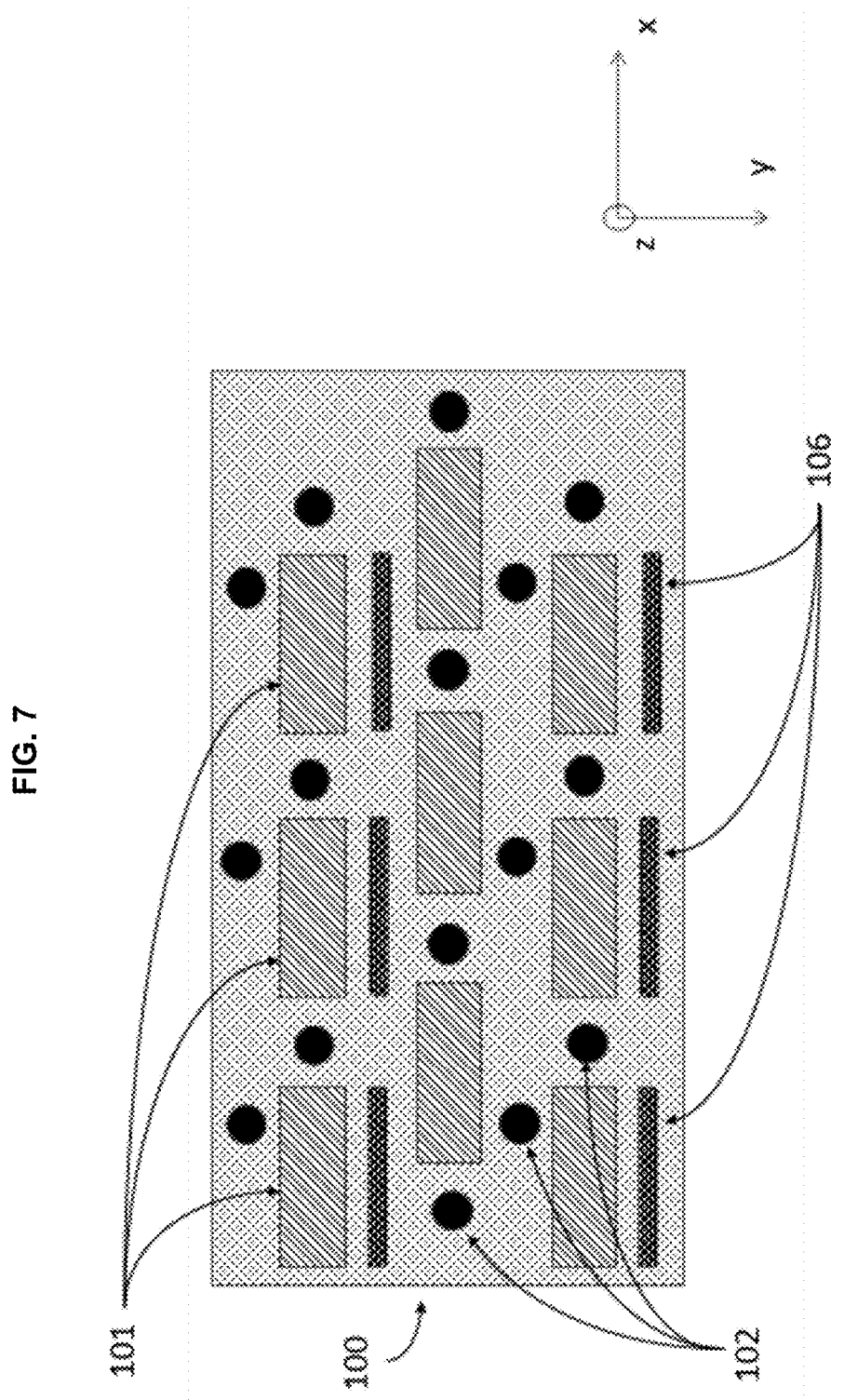
FIG. 7 shows a layout view of an exemplary embodiment of an integrated MUT and ASIC system using hybrid contacts in FIG. 1B with added hybrid contacts.
Figure 8:
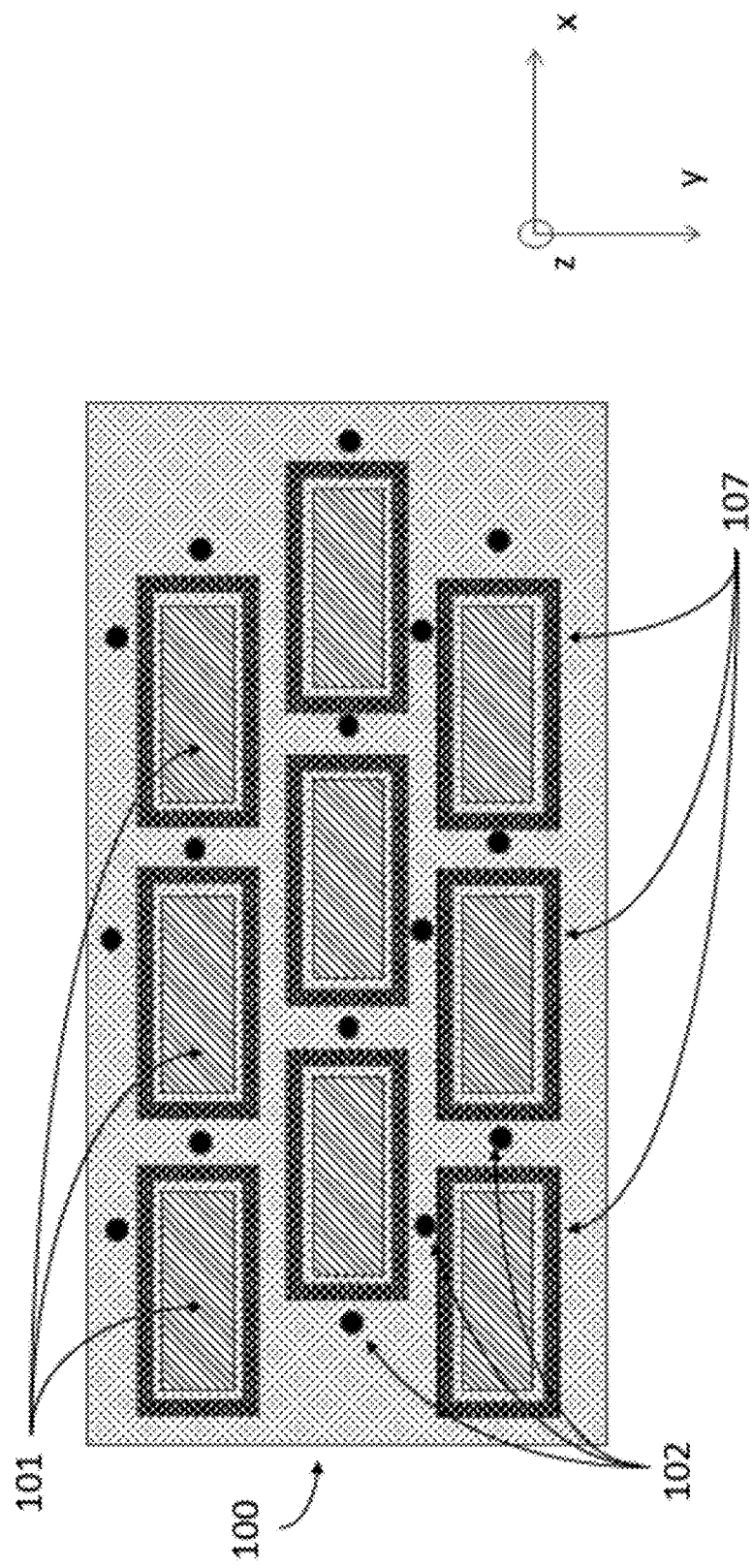
FIG. 8 shows a layout view of an exemplary embodiment of an integrated MUT and ASIC system using hybrid contacts in FIG. 1B with added hybrid contacts.

In some embodiments, the hybrid contacts may not be of a uniform layout shape. Instead, in some embodiments, the hybrid contacts may be with a variety of shapes that facilitate improvement of MUT performance. As an example, FIG. 7 illustrates added elongated contacts 106 that are longer (e.g., along x axis) and slender (e.g., along y axis). The contact 106 can be hybrid contact or mechanical contact. In this embodiment, such elongated contacts provide a large fixed boundary condition thus improving the MUT performance. As another example, one or more of the membranes 101 of the MUT array 100 may be enclosed at least partly by the annular hybrid contacts 107 illustrated in FIG. 8. In these embodiments, the annular contacts and the elongated contacts are hybrid. In some embodiments, the annular contacts and the elongated contacts are electrical and/or mechanical.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

As used herein A and/or B encompasses one or more of A or B, and combinations thereof such as A and B. It will be understood that although the terms "first," "second," "third," etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present disclosure.

The terminology used herein is for the purpose of describing particular embodiments only and is not intended to limit the present disclosure. As used herein, the singular forms "a," "an," and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

As used in this specification and the claims, unless otherwise stated, the term "about," and "approximately," or "substantially" refers to variations of less than or equal to +/−0.1%, +/−1%, +/−2%, +/−3%, +/−4%, +/−5%, +/−6%, +/−7%, +/−8%, +/−9%, +/−10%, +/−11%, +/−12%, +/−14%, +/−15%, or +/−20%, including increments therein, of the numerical value depending on the embodiment. As a non-limiting example, about 100 meters represents a range of 95 meters to 105 meters (which is +/−5% of 100 meters), 90 meters to 110 meters (which is +/−10% of 100 meters), or 85 meters to 115 meters (which is +/−15% of 100 meters) depending on the embodiments.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An ultrasonic transducer system with hybrid contacts comprising:
   a) a micromachined ultrasonic transducer (MUT) element comprising a substrate and a membrane;
   b) an electrical circuitry comprising an application specific integrated circuit (ASIC); and c) one or more hybrid contacts configured to couple the transducer element to the ASIC, wherein the one or more hybrid contacts are each capable of providing an electrical connection between the MUT and the ASIC and a mechanical connection that provides structural rigidity to the transducer system, wherein each of the one or more hybrid contacts comprises a cylindrical shape such that the hybrid contacts comprise a single diameter from a surface of the ASIC to a top of the contact, wherein a ratio of a height of the hybrid contact to the diameter of the hybrid contact is between approximately 1:2 to 2:1, wherein the shape and placement of the hybrid contacts are designed to enhance dynamics of the ultrasonic transducer system.

2. The ultrasonic transducer system of claim 1, further comprising:
a) a second ultrasonic transducer element comprising a second substrate and a second membrane;
b) a second electrical circuitry; and
c) one or more additional contacts connected to the second ultrasonic transducer element and the second electrical circuitry, wherein the one or more additional contacts are one or more of: electrical contacts, mechanical contacts, or hybrid contacts.

3. The ultrasonic transducer system of claim 2, wherein the ultrasonic transducer element and the second ultrasonic transducer element form a two-dimensional array with a plurality of additional ultrasonic transducer elements.

4. The ultrasonic transducer system of claim 1, further comprising one or more contacts that are electrical contacts only or mechanical contacts only.

5. The ultrasonic transducer system of claim 1, wherein the one or more hybrid contacts are configured to provide electrical connection and mechanical connection simultaneously or electrical connection but not mechanical connection when a predetermined threshold condition has been met.

6. The ultrasonic transducer system of claim 1, wherein the one or more hybrid contacts comprise an aspect ratio of height to effective diameter of approximately 1:1.

7. The ultrasonic transducer system of claim 1, further comprising an array of contacts comprising one or more of: a range of spacing of the one or more contacts of no less than about 5 μm, a minimum number of 2 of electrical contacts within the ultrasonic transducer element, a maximum number of 4 of electrical contacts within the ultrasonic transducer element, a minimum number of 2 of mechanical contacts within the ultrasonic transducer element, a maximum number of 10 of mechanical contacts within the ultrasonic transducer element, a minimum number of hybrid contacts within the ultrasonic transducer element, and a maximum number of hybrid contacts within the ultrasonic transducer element.

8. The ultrasonic transducer system of claim 7, further comprising:
a) arranging the array of contacts to be symmetrical about an axis of the membrane; and
b) arranging the array of contacts to surround the membrane, or their combination.

9. The ultrasonic transducer system of claim 6, wherein the shape of the one or more hybrid contacts is an annular shape that provides a fixed boundary condition that improves performance of the ultrasonic transducer element.

10. The ultrasonic transducer system of claim 8, wherein a symmetrical contact arrangement enables a higher maximum surface velocity than that of an asymmetrical contact arrangement, and wherein the maximum surface velocity of the membrane is directly related to a maximum pressure output achievable with the ultrasonic transducer element.

11. The ultrasonic transducer system of claim 1, wherein the aspect ratio of height to diameter of approximately 0.6:1 to 1.5:1.

12. The ultrasonic transducer system of claim 1, wherein the diameter of the hybrid contacts is approximately 50 μm and the height of the hybrid contacts is approximately 50 μm.

13. A method of improving performance of an ultrasonic transducer system using hybrid contacts, comprising:
a) obtaining an ultrasonic transducer system, the ultrasonic transducer system comprising:
an ultrasonic transducer element comprising a substrate and a membrane; and
an electrical circuitry connected to the ultrasonic transducer element, the electrical circuitry comprising an application specific integrated circuit (ASIC);
b) obtaining one or more hybrid contacts, the one or more hybrid contacts each being capable of providing an electrical connection and a mechanical connection, wherein the hybrid contacts comprise a cylindrical shape with an aspect ratio of height to diameter of approximately 1:2 to 2:1 and wherein a size of the hybrid contacts is larger than necessary to provide the electrical connection in order to provide the mechanical connection that provides structural stability to the ultrasonic transducer system to enhance dynamics of the ultrasonic transducer system; and
c) adding the one or more hybrid contacts to the ultrasonic transducer system, comprising:
arranging the one or more hybrid contacts with respect to the membrane; and
coupling the transducer element to the ASIC through the hybrid contacts.

14. The method of claim 13, wherein the ultrasonic transducer element is a micromachined ultrasonic transducer (MUT) element.

15. The method of claim 13, wherein the ultrasonic transducer system further comprises:
a second ultrasonic transducer element comprising a second substrate and a second membrane;
a second electrical circuitry; and
one or more additional contacts connected to the second ultrasonic transducer element and the second electrical circuitry,
wherein the one or more additional contacts are one or more of: electrical contacts, mechanical contacts, or hybrid contacts.

16. The method of claim 15, wherein the ultrasonic transducer element and the second ultrasonic transducer element form a two-dimensional array with a plurality of additional ultrasonic transducer elements.

17. The method of claim 13, wherein the one or more hybrid contacts are configured to provide electrical connection and mechanical connection simultaneously or electrical connection but not mechanical connection when a predetermined threshold condition has been met.

18. The method of claim 13, wherein the one or more hybrid contacts comprise: a range of diameter, a range of height, a range of aspect ratio, and comprise a shape, wherein (i) the range of diameter is about 5 μm to about 100 μm, (ii) the range of height is about 0 μm to about 300 μm, (iii) the aspect ratio of height to effective diameter is less than about 60:1, or (iv) the shape is selected from the group consisting of a cylinder, an annular shape, and an elongated shape.

19. The method of claim 13, further comprising an array of contacts comprising one or more of: a range of spacing of the one or more contacts to the membrane, a minimum number of electrical contacts within the ultrasonic transducer element, a maximum number of electrical contacts within the ultrasonic transducer element, a minimum number of mechanical contacts within the ultrasonic transducer element, a maximum number of mechanical contacts within the ultrasonic transducer element, a minimum number of hybrid contacts within the ultrasonic transducer element, a maximum number of hybrid contacts within the ultrasonic transducer element.

20. The method of claim 13, further comprising:
   a) arranging the array of contacts to be symmetrical about an axis of the membrane; and
   b) arranging the array of contacts to surround the membrane, or their combination.

\* \* \* \* \*